US00PP35626P2

(12) United States Plant Patent
Bernuetz

(10) Patent No.: US PP35,626 P2
(45) Date of Patent: Jan. 30, 2024

(54) ***XEROCHRYSUM* PLANT NAMED 'BONXER 1856'**

(50) Latin Name: *Xerochrysum bracteatum*
Varietal Denomination: Bonxer 1856

(71) Applicant: Andrew Bernuetz, Glenbrook (AU)

(72) Inventor: Andrew Bernuetz, Glenbrook (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/208,861

(22) Filed: Jun. 12, 2023

(51) Int. Cl.
*A01H 5/02* (2018.01)
*A01H 6/14* (2018.01)

(52) U.S. Cl.
USPC ..... Plt./359

(58) Field of Classification Search
USPC ..... Plt./263.1, 359
See application file for complete search history.

(56) References Cited

U.S. PATENT DOCUMENTS

PP29,067 P2 * 3/2018 Bowyer ..... A01H 6/14
Plt./359

* cited by examiner

*Primary Examiner* — Karen M Redden
(74) *Attorney, Agent, or Firm* — C. Anne Whealy

(57) ABSTRACT

A new and distinct cultivar of *Xerochrysum* plant named 'Bonxer 1856', characterized by its upright and uniformly mounding plant habit; vigorous growth habit; freely flowering habit; inflorescences with bright red-colored involucral bracts; and strong peduncles that hold the inflorescences above the foliar plane.

1 Drawing Sheet

Figure 1:
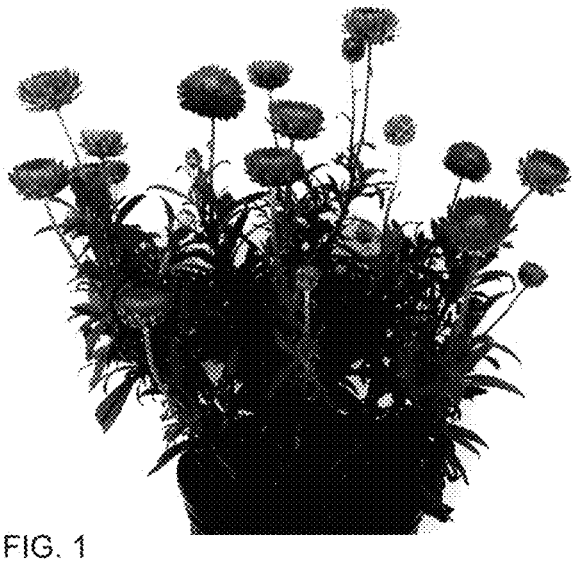

Botanical designation: *Xerochrysum bracteatum.*
Cultivar denomination: 'BONXER 1856'.

BACKGROUND OF THE INVENTION

The present invention relates to a new and distinct cultivar of *Xerochrysum* plant, botanically known as *Xerochrysum bracteatum*, and hereinafter referred to by the name 'Bonxer 1856'.

The new *Xerochrysum* plant is a product of a planned breeding program conducted by the Inventor in Yellow Rock, New South Wales, Australia. The objective of the breeding program is to create and develop new upright and uniformly mounded *Xerochrysum* cultivars with numerous attractive inflorescences.

The new *Xerochrysum* plant originated from a cross-pollination by the Inventor in July, 2017 of a proprietary selection of *Xerochrysum bracteatum* identified as code number 16-55, not patented, as the female, or seed, parent with a proprietary selection of *Xerochrysum bracteatum* identified as code number 16-68, not patented, as the male, or pollen, parent. The new *Xerochrysum* plant was discovered and selected by the Inventor as a single flowering plant within the progeny of the stated cross-pollination in a controlled greenhouse environment in Yellow Rock, New South Wales, Australia on Feb. 16, 2018.

Asexual reproduction of the new *Xerochrysum* plant by terminal cuttings in a controlled greenhouse environment in Yellow Rock, New South Wales, Australia since February, 2018, has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxer 1856'. These characteristics in combination distinguish 'Bonxer 1856' as a new and distinct *Xerochrysum* plant:

1. Upright and uniformly mounding plant habit.
2. Vigorous growth habit.
3. Freely flowering habit.
4. Inflorescences with bright red-colored involucral bracts.
5. Strong peduncles that hold the inflorescences above the foliar plane.

In side-by-side comparisons, plants of the new *Xerochrysum* differ primarily from plants of the female parent selection in involucral bract color as inflorescences of plants of the new *Xerochrysum* have bright red-colored involucral bracts whereas inflorescences of plants of the female parent selection have orange-colored involucral bracts.

In side-by-side comparisons, plants of the new *Xerochrysum* differ primarily from plants of the male parent selection in involucral bract color as inflorescences of plants of the new *Xerochrysum* have bright red-colored involucral bracts whereas inflorescences of plants of the male parent selection have pink-colored involucral bracts.

Plants of the new *Xerochrysum* can be compared to plants of the *Bracteantha bracteata* 'Bonxero 148', disclosed in U.S. Plant Pat. No. 30,398. In side-by-side comparisons, plants of the new *Xerochrysum* differ primarily from plants of 'Bonxero 148' in the following characteristics:

1. Plants of the new *Xerochrysum* are more freely branching than plants of 'Bonxero 148'.

2. Plants of the new *Xerochrysum* have smaller leaves than plants of 'Bonxero 148'.
3. Plants of the new *Xerochrysum* have smaller inflorescences than plants of 'Bonxero 148'.
4. Inflorescences of plants of the new *Xerochrysum* have bright red-colored involucral bracts whereas inflorescences of plants of 'Bonxero 148' have yellow-colored involucral bracts.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph at the top of the sheet (FIG. 1) is a side perspective view of a typical flowering plant of 'Bonxer 1856' grown in a container.

Figure 2:
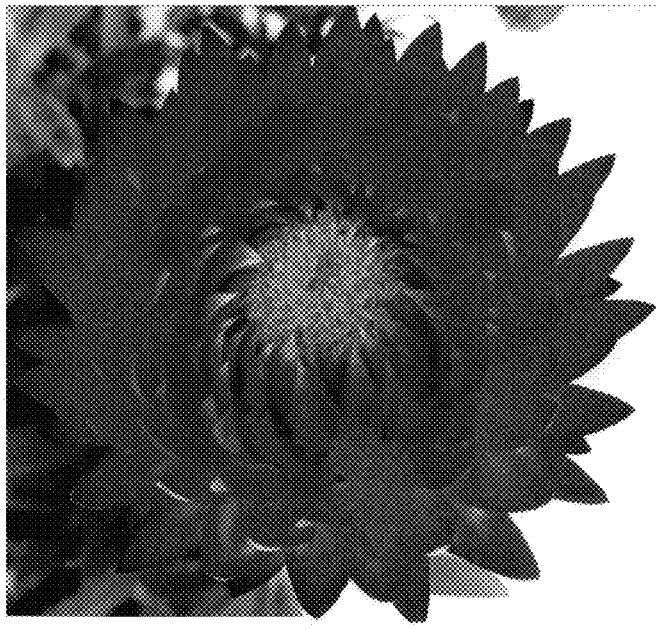

The photograph at the bottom of the sheet (FIG. 2) is a close-up view of a typical inflorescence of 'Bonxer 1856'.

DETAILED BOTANICAL DESCRIPTION

The aforementioned photographs and following observations and measurements describe plants grown during the early summer in 24-cm containers in an outdoor nursery in Higashiomi, Shiga, Japan and under conditions and practices which approximate those generally used in commercial *Xerochrysum* production. During the production of the plants, day temperatures averaged 23 C and night averaged 13 C. Measurements and numerical values represent averages for typical flowering plants. Plants were four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Xerochrysum bracteatum* 'Bonxer 1856'.

Parentage:

*Female, or seed, parent*.—Proprietary selection of *Xerochrysum bracteatum* identified as code number 16-56, not patented.

*Male, or pollen, parent*.—Proprietary selection of *Xerochrysum bracteatum* identified as code number 16-68, not patented.

Propagation:

*Type*.—Terminal vegetative cuttings.

*Time to initiate roots, summer*.—About seven days at temperatures about 18 C to 21 C.

*Time to initiate roots, winter*.—About ten days at temperatures about 18 C to 21 C.

*Time to produce a rooted cutting, summer*.—About three weeks at temperatures about 18 C to 21 C.

*Time to produce a rooted cutting, winter*.—About four weeks at temperatures about 18 C to 21 C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Upright and uniformly mounding plant habit with inflorescences held above the foliage on strong peduncles; vigorous growth habit.

*Plant height*.—About 46 cm.

*Plant diameter or spread*.—About 52 cm.

*Lateral branches*.—Quantity per plant: Freely branching habit with about 13 lateral branches develop per plant. Length: About 35.8 cm. Diameter: About 4.1 mm. Internode length: About 1.7 cm. Aspect: Upright to somewhat outwardly. Strength: Strong. Texture: Rough, moderately pubescent. Color: Close to 137B.

*Leaf description*.—Arrangement: Alternate, simple; sessile. Length: About 6.1 cm. Width: About 1.2 cm. Shape: Linear. Apex: Acuminate. Base: Attenuate. Margin: Entire; not undulate to slightly undulate. Texture, upper and lower surfaces: Rough, moderately pubescent. Venation pattern: Pinnate; reticulate. Color: Developing leaves, upper surface: Close to NN137C. Developing leaves, lower surface: Close to 138A. Fully expanded leaves, upper surface: Close to NN137A; venation, close to 138A. Fully expanded leaves, lower surface: Close to NN137C; venation, close to 138B.

Inflorescence description:

*Appearance*.—Terminal double-type inflorescence form with numerous deltoid involucral bracts; involucral bracts and disc florets developing acropetally on a capitulum; inflorescences positioned above the foliar plane on strong peduncles; inflorescences face mostly upright.

*Flowering habit*.—Freely flowering habit; about 36 inflorescence buds and inflorescences per plant.

*Fragrance*.—None detected.

*Time to flower*.—In Japan, plants begin to flower about 21 weeks after planting and in the garden, plants flower continuously from the spring through the autumn.

*Post-production longevity*.—Inflorescences maintain good substance for about seven to ten days on the plant; inflorescences persistent.

*Inflorescence buds*.—Height: About 1.8 cm. Diameter: About 1.7 cm. Shape: Ovoid with acute apex. Color: Distally, close to N34A and proximally, close to 150D.

*Inflorescence size*.—Diameter: About 5.6 cm. Depth (height): About 2.2 cm. Disc diameter: About 1.9 cm. Disc height: About 7.1 mm.

*Receptacles*.—Diameter: About 2.5 cm. Height: About 5.5 mm. Color: Close to 150D.

*Involucral bracts*.—Quantity per inflorescence and arrangement: About 225 arranged in numerous whorls; bracts imbricate. Length: About 1.6 cm. Width: About 6 mm. Shape: Deltoid. Apex: Acuminate. Base: Truncate. Margin: Entire. Texture, upper and lower surfaces: Smooth, glabrous; papery; durable. Orientation: Initially upright becoming more outward with development. Color: When opening and fully opened, upper surface: Close to 34A and towards the margins, close to N34A; color does not change with subsequent development. When opening and fully opened, lower surface: Close to 31A and towards the margins, close to 34B; color does not change with subsequent development.

*Disc florets*.—Quantity per inflorescence and arrangement: Numerous disc florets are spirally arranged in the center of the receptacle. Length: About 1 cm. Diameter, distally: About 2 mm. Diameter, proximally: About 0.8 mm. Shape: Tubular; apex dentate, five-pointed. Texture, inner and outer surfaces: Smooth, glabrous. Color: When developing, inner and outer surfaces: Close to 17A. Fully developed, inner and outer surfaces: Apex: Close to 17A. Midsection: Close to 150C. Base: Close to 150D.

*Peduncles*.—Length: About 5.8 cm. Diameter: About 2.8 mm. Strength: Strong. Aspect: Upright to somewhat outwardly. Texture: Rough, pubescent. Color: Close to 138C.

*Reproductive organs*.—Androecium: Quantity per disc floret: About five. Filament length: About 2.5 mm. Filament color: Close to 150D. Anther size: About 0.8 mm by 2.6 mm. Anther shape: Linear. Anther color: Close to 150D. Pollen amount: None observed. Gynoecium: Quantity per disc floret: One. Pistil length: About 9.5 mm. Stigma shape: Biparted. Stigma color: Close to 17B. Style color: Close to 150D. Ovary color: Close to 155A.

*Seeds and fruits*.—To date, seed and fruit production has not been observed on plants of the new *Xerochrysum*.

Pathogen & pest resistance: To date, plants of the new *Xerochrysum* have not been observed to be resistant to pathogens and pests common to *Xerochrysum* plants.

Temperature tolerance: Plants of the new *Xerochrysum* have been observed to tolerate temperatures ranging from about 1 C to about 35 C.

It is claimed:

1. A new and distinct *Xerochrysum* plant named 'Bonxer 1856' as illustrated and described.

* * * * *